US011951174B2

(12) United States Patent
Singh

(10) Patent No.: US 11,951,174 B2
(45) Date of Patent: Apr. 9, 2024

(54) THERAPEUTICS DIRECTED AGAINST CORONAVIRUS

(71) Applicant: Singh Biotechnology, LLC, Lutz, FL (US)

(72) Inventor: Sunanda Singh, Lutz, FL (US)

(73) Assignee: Singh Biotechnology, LLC, Lutz, FL (US)

( * ) Notice: Subject to any disclaimer, the term of this patent is extended or adjusted under 35 U.S.C. 154(b) by 0 days.

(21) Appl. No.: 18/301,761

(22) Filed: Apr. 17, 2023

(65) Prior Publication Data

US 2023/0277681 A1 Sep. 7, 2023

Related U.S. Application Data

(63) Continuation of application No. 17/579,455, filed on Jan. 19, 2022, now abandoned.

(60) Provisional application No. 63/139,480, filed on Jan. 20, 2021.

(51) Int. Cl.

| | |
|---|---|
| *A61K 47/68* | (2017.01) |
| *A61K 38/16* | (2006.01) |
| *A61K 38/17* | (2006.01) |
| *A61K 47/64* | (2017.01) |
| *A61P 31/14* | (2006.01) |

(52) U.S. Cl.
CPC ........ *A61K 47/6811* (2017.08); *A61K 38/162* (2013.01); *A61K 38/177* (2013.01); *A61K 47/643* (2017.08); *A61K 47/644* (2017.08); *A61P 31/14* (2018.01)

(58) Field of Classification Search
CPC .............. A61K 47/6811; A61K 47/643; A61K 38/177; A61K 38/162; A61K 47/644
See application file for complete search history.

(56) References Cited

U.S. PATENT DOCUMENTS

| | | | |
|---|---|---|---|
| 7,396,914 | B2 | 7/2008 | Ambrosino et al. |
| 7,491,397 | B2 | 2/2009 | Chong et al. |
| 7,527,967 | B2 | 5/2009 | Chao et al. |
| 7,888,102 | B2 | 2/2011 | Brink et al. |
| 8,080,642 | B2 | 12/2011 | Vilalta et al. |
| 8,241,864 | B2 | 8/2012 | Loibner et al. |
| 8,541,003 | B2 | 9/2013 | Anderson et al. |
| 8,586,319 | B2 | 11/2013 | Schuster et al. |
| 9,884,895 | B2 | 2/2018 | Baric et al. |
| 10,443,049 | B2 | 10/2019 | Batlle et al. |
| 2005/0113298 | A1 | 5/2005 | Farzan et al. |
| 2005/0282154 | A1 | 12/2005 | Farzan et al. |
| 2009/0304683 | A1 | 12/2009 | Dimitrov et al. |
| 2016/0376321 | A1 | 12/2016 | Hotez et al. |
| 2019/0241633 | A1 | 8/2019 | Fotin-Mleczek et al. |
| 2021/0246170 | A1* | 8/2021 | Langedijk ............ C07K 14/005 |

FOREIGN PATENT DOCUMENTS

| | | | | |
|---|---|---|---|---|
| WO | 2006071250 | A3 | 1/2007 | |
| WO | WO-2021213520 | A1 * | 10/2021 | .............. A61P 11/00 |

OTHER PUBLICATIONS

SEQ ID No. 2 in WO 2021213520 A1, Apr. 24, 2020, enclosed pp. 1-4.*
Li, Yujun, et al., SARS-COV-2 and Three Related Coronaviruses Utilize Multiple ACE2 Orthologs and Are Potently Blocked by an Improved ACE2-Ig, Journal of Virolology, Nov. 2020, vol. 94, Issue 22, e-01283-20, pp. 1-14.
Ren, Wenlin, et al., Recombinant SARS-CoV-2 spike S1-Fc fusion protein induced high levels of neutralizing responses in non-human primates, Vaccine, Jun. 24, 2020, vol. 38, pp. 5653-5658.
USPTO, Written Opinion issued by the International Searching Authority in related International Patent Application No. PCT/US2022/02884 dated Apr. 8, 2022. (6 pages).
USPTO, International Search Report (ISR) issued by the International Searching Authority in related International Patent Application No. PCT/US2022/02884 dated Apr. 8, 2022. (3 pages).
Chan, Kui K et. al., "Engineering human ACE2 to optimize binding to the spike protein of SARS coronavirus 2," www,sciencemag.org, Science, Aug. 4, 2020, pp. 1-11, (11 pages).
Lan, Jun, et. al., "Structure of the SARS-CoV-2 spike receptor-binding domain bound to the ACE2 receptor," NatureResearch, May 2020, vol. 581, pp. 215-230 (16 pages).
Yan, Renhong, et al., "Structural basis for the recognition of SARS-CoV-2 by full-length human ACE2," Science, Mar. 27, 2020, vol. 367, pp. 1444-1448, 5 pages.
Yuan, Meng, et. al., "A highly conserved cryptic epitope in the receptor binding domains of SARS-CoV-2 and SARS-CoV," Science, May 8, 2020, vol. 368, pp. 630-633, 4 pages.

* cited by examiner

*Primary Examiner* — Li N Komatsu

(74) *Attorney, Agent, or Firm* — Laura M. King; Matrix Law Group, LLP

(57) ABSTRACT

This invention provides compositions and methods to treat, prevent, and diagnose viral infections. The methods provided herein involve administering polypeptides of the invention to a subject in need thereof. The viral infections can be caused by a coronavirus such as SARS-CoV-1, SARS-CoV-2 or a variant thereof. It is contemplated that the polypeptide can be further linked to a compound, wherein the compound extends the serum half-life of the polypeptide.

5 Claims, 3 Drawing Sheets

Specification includes a Sequence Listing.

FIG. 4

THERAPEUTICS DIRECTED AGAINST CORONAVIRUS

CROSS REFERENCE TO RELATED APPLICATIONS

This application is a continuation of U.S. patent application Ser. No. 17/579,455, filed on Jan. 19, 2022, which claims the benefit of U.S. Provisional Patent Application No. 63/139,480, filed on Jan. 20, 2021, the contents of which are incorporated herein by reference in their entirety.

SEQUENCE LISTING

The present application is being filed along with a Sequence Listing in electronic format. The Sequence Listing is provided as a file titled "sequence_listing.xml," created Apr. 17, 2023, and is 7,000 bytes in size. The information in the electronic format of the Sequence Listing is incorporated herein by reference in its entirety.

BACKGROUND

Severe acute respiratory syndrome (SARS) is an acute infectious disease that spreads mainly via the respiratory route. SARS can be caused by a coronavirus (SARS-CoV or SARS-CoV-1), which is an enveloped, positive-sense, single-stranded RNA virus which infects the epithelial cells within the lungs. A similar coronavirus, SARS-CoV-2, has been identified as the etiological agent that causes COVID-19. With the COVID-19 pandemic, it is crucial to develop therapeutic and prophylactic agents.

A zinc-containing metallopeptidase named angiotensin-converting enzyme 2 (ACE2) has been identified as the functional receptor for entry of SARS-CoV-1 and SARS-CoV-2 into cells. ACE2 is located on the surface of endothelial and other cells. ACE2 mRNA is known to be present in various organs, and is highly expressed in renal, cardiovascular, and gastrointestinal tissues. ACE2 is a single-pass type I membrane protein, with an enzymatically active domain exposed on the surface of cells. The extracellular domain of ACE2 is cleaved from the transmembrane domain by another enzyme known as sheddase, and the resulting soluble protein is released into the blood stream and ultimately excreted into urine.

The coronavirus spike (S) protein mediates receptor binding as well as fusion of the viral and cellular membrane. The S protein extends from the viral membrane and is arranged as trimers on the surface of the virion. The coronavirus S protein is divided into two domains: S1 and S2. The S1 domain mediates receptor binding, and the S2 mediates downstream membrane fusion. The S1 protein binds to cellular proteins, including the ACE2 receptor. Variant coronaviruses containing one or more mutations in the S1 protein have been discovered that are associated with increased transmissibility of the virus.

Compounds targeting the interaction between the S1 protein and the ACE2 receptor may offer protection against the SARS-CoV infection. Infection begins after the S1 protein attaches to its complementary host cell receptor. In particular, a region of S1 protein called the receptor binding domain (RBD) is responsible for host cell receptor attachment. After attachment, a host cell protease cleaves and activates the receptor attached S1 protein, which allows the virus to enter the host cell by endocytosis or direct fusion of the viral envelope with the host membrane.

It is contemplated that soluble S1 and/or RBD proteins can be administered to patients infected with SARS-CoV-1 and SARs-CoV-2 and variants thereof. The soluble S1 and/or RBD proteins bind to the ACE2 receptor, and competes with the viral S1 and/or RBD proteins to bind ACE2 host cell receptors. This results in competitive blocking of the ability of the virus to infect cells. Once the concentration of soluble S1 and/or RBD protein reaches a sufficient concentration in vivo, infection with SARS-CoV-1 and SARS-CoV-2 and variants thereof is reduced or prevented. The soluble S1 and/or RBD proteins can be administered intravenously and/or via nebulizer to treat patients infected with SARS-CoV-1 and/or SARS-CoV-2 and variants thereof.

In an alternative embodiment of the invention, all or a portion of the extracellular domain of the ACE2 receptor can be used as a therapeutic. ACE2 can be administered intravenously and/or via nebulizer to treat patients infected with SARS-CoV-1 and/or SARS-CoV-2 and variants thereof. ACE2 will bind to the RBD region of S1 attached to the virus and prevent it from binding to the cellular ACE2 receptor, thus preventing or reducing viral infection. This approach of using soluble recombinant receptors that bind to SARS-CoV-1 and SARS-CoV-2 can be used with receptors other than ACE2 receptors.

SUMMARY

One embodiment of the present invention involves a method for treating infection with severe acute respiratory syndrome coronavirus 1 (SARS-CoV-1), severe acute respiratory syndrome coronavirus 2 (SARS-CoV-2) or a variant thereof, wherein the method comprises administering to a subject in need thereof a composition comprising a first polypeptide and a second polypeptide, wherein the first polypeptide consists of SEQ ID NO:1 or SEQ ID NO:1 linked to albumin, transferrin, or Fc-portion of an antibody, and the second polypeptide comprises SEQ ID NO:2. In one aspect, the composition further comprises a pharmaceutically acceptable carrier or excipient. In another aspect, the composition is administered by a route selected from the group consisting of oral, intravenous, intramuscular, subcutaneous, and transdermal administration. In another aspect, the second polypeptide is further linked to a compound that extends the serum half-life of the second polypeptide. The compound can be albumin, transferrin, or Fc-portion of an antibody.

DRAWINGS

These and other features, aspects, and advantages of the present invention will become better understood with regard to the following description, appended claims, and accompanying drawings where:

FIG. 4 depicts the percent of inhibition of ACE2 binding to S1 from different viral variants.

DESCRIPTION

Figure 1:
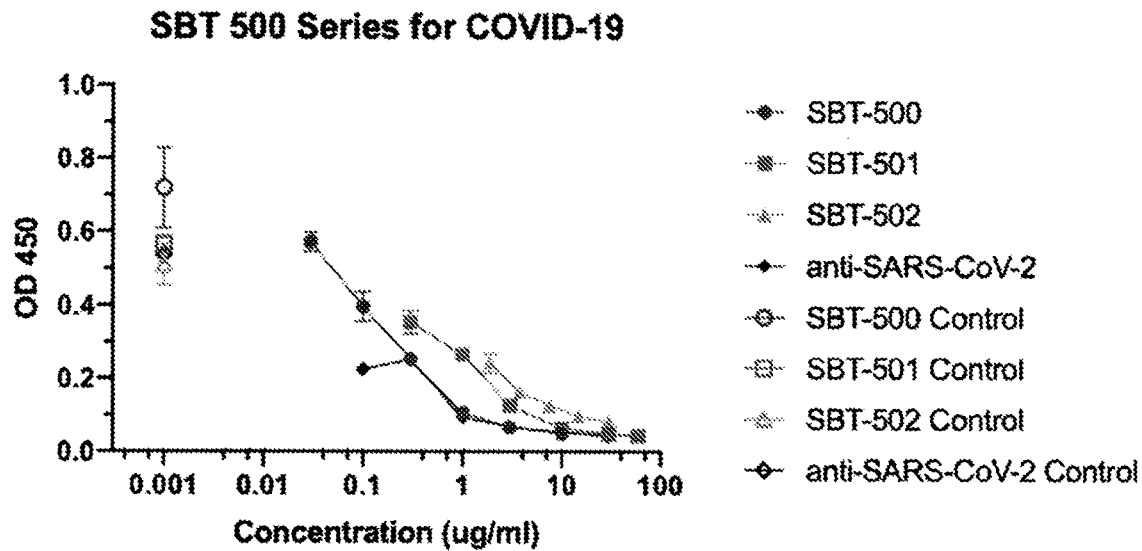
FIG. 1 depicts the average absorbance values from Table 3.

Provided herein are compositions and methods for treating, preventing and diagnosing viral infections, in particular for treating, preventing, and diagnosing coronavirus infections.

As used herein, the following terms and variations thereof have the meanings given below, unless a different meaning is clearly intended by the context in which such term is used.

The terms "a," "an," and "the" as used herein are to be construed to cover both the singular and the plural unless their usage in context indicates otherwise.

The term "antigenic determinant" refers to the epitope on the antigen recognized by the antigen-binding molecule (such as an sdAb or polypeptide of the invention) and more in particular by the antigen-binding site of the antigen-binding molecule. The terms "antigenic determinant" and "epitope" may also be used interchangeably. An amino acid sequence that can bind to, that has affinity for and/or that has specificity for a specific antigenic determinant, epitope, antigen or protein is said to be "against" or "directed against" the antigenic determinant, epitope, antigen or protein.

As used herein, the term "antiviral polypeptide" means any polypeptide that can prevent, reduce, or treat viral infections.

As used herein, the term "comprise" and variations of the term, such as "comprising" and "comprises," are not intended to exclude other additives, components, integers or steps.

It is contemplated that the polypeptides and proteins described herein can contain so-called "conservative" amino acid substitutions, which can generally be described as amino acid substitutions in which an amino acid residue is replaced with another amino acid residue of similar chemical structure, and which has little or essentially no influence on the function, activity or other biological properties of the polypeptide. Conservative amino acid substitutions are well known in the art. Conservative substitutions are substitutions in which one amino acid within the following groups (a)-(e) is substituted by another amino acid within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp. Other conservative substitutions include: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Be into Leu or into Val; Leu into Be or into Val; Lys into Arg, into Gln or into Glu; Met into Leu, into Tyr or into Be; Phe into Met, into Leu or into Tyr; Ser into Thr; Thr into Ser; Trp into Tyr; Tyr into Trp; and/or Phe into Val, into Ile or into Leu.

As used herein, an "isolated" nucleic acid or amino acid has been separated from at least one other component with which it is usually associated, such as its source or medium, another nucleic acid, another protein/polypeptide, another biological component or macromolecule or contaminant, impurity or minor component.

The term "mammal" is defined as an individual belonging to the class Mammalia and includes, without limitation, humans, domestic and farm animals, and zoo, sports, and pet animals, such as cows, horses, sheep, dogs and cats.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field. Preferred examples of such carriers or diluents include, but are not limited to, water, saline, Ringer's solutions, dextrose solution, PBS (phosphate-buffered saline), and 5% human serum albumin. Liposomes, cationic lipids and non-aqueous vehicles such as fixed oils may also be used. The use of such media and agents for pharmaceutically active substances is well known in the art. Except insofar as any conventional media or agent is incompatible with a therapeutic agent as defined above, use thereof in the composition of the present invention is contemplated.

A "quantitative immunoassay" refers to any means of measuring an amount of antigen present in a sample by using an antibody. Methods for performing quantitative immunoassays include, but are not limited to, enzyme-linked immunosorbent assay (ELISA), specific analyte labeling and recapture assay (SALRA), liquid chromatography, mass spectrometry, fluorescence-activated cell sorting, and the like.

The term "solution" refers to a composition comprising a solvent and a solute, and includes true solutions and suspensions. Examples of solutions include a solid, liquid or gas dissolved in a liquid and particulates or micelles suspended in a liquid.

The term "specificity" refers to the number of different types of antigens or antigenic determinants to which a particular antigen-binding molecule or antigen-binding protein molecule can bind. The specificity of an antigen-binding protein can be determined based on affinity and/or avidity. The affinity, represented by the equilibrium constant for the dissociation of an antigen with an antigen-binding protein (KD), is a measure for the binding strength between an antigenic determinant and an antigen-binding site on the antigen-binding protein: the lesser the value of the KD, the stronger the binding strength between an antigenic determinant and the antigen-binding molecule (alternatively, the affinity can also be expressed as the affinity constant (KA), which is 1/KD). As will be clear to one of skill in the art, affinity can be determined depending on the specific antigen of interest. Avidity is the measure of the strength of binding between an antigen-binding molecule and the antigen. Avidity is related to both the affinity between an antigenic determinant and its antigen binding site on the antigen-binding molecule and the number of pertinent binding sites present on the antigen-binding molecule. Specific binding of an antigen-binding protein to an antigen or antigenic determinant can be determined by any known manner, such as, for example, Scatchard analysis and/or competitive binding assays, such as radioimmunoassays (RIA), enzyme immunoassays (EIA) and sandwich competition assays.

As used herein, the term "recombinant" or "recombinant protein" refers to the use of genetic engineering methods (for example, cloning, and amplification) used to produce the proteins and polypeptides of the invention.

The term "S protein" or "S1" refers to the spike glycoprotein encoded by SARS-CoV. "Protein" is used interchangeably with "polypeptide." As used herein, SBT-500 (SEQ ID NO:1) refers to a recombinant RBD of the S1 protein (encoded by the SARS-CoV-2 (2019-nCoV) Spike Protein (RBD) (YP_009724390.1) (Arg319-Phe541) expressed with a polyhistidine tag at the C-terminus) (Sino Biological US Inc., Wayne, PA). The sequence is as follows:

SEQ ID NO: 1

```
RVQPTESIVRFPNITNLCPFGEVFNATRFASVYAWNRKRISNCVADYSVL

YNSASFSTFKCYGVSPTKLNDLCFTNVYADSFVIRGDEVRQIAPGQTGKI
```

-continued
ADYNYKLPDDFTGCVIAWNSNNLDSKVGGNYNYLYRLFRKSNLKPFERDI

STEIYQAGSTPCNGVEGFNCYFPLQSYGFQPTNGVGYQPYRVVVLSFELL

HAPATVCGPKKSNLVKNKCVNFAHHHHHHHHHH

SBT-501 (SEQ ID NO:2) refers to the entire recombinant S1 protein (encoded by SARS-CoV-2 spike protein S1 Subunit (YP_009724390.1) DNA sequence (Val16-Arg685) expressed with a polyhistidine tag at the C-terminus) (Sino Biological US Inc., Wayne, PA). The sequence is as follows:

SEQ ID NO: 2
VNLTTRTQLPPAYTNSFTRGVYYPDKVFRSSVLHSTQDLFLPFFSNVTWF

HAIHVSGTNGTKRFDNPVLPFNDGVYFASTEKSNIIRGWIFGTTLDSKTQ

SLLIVNNATNVVIKVCEFQFCNDPFLGVYYHKNNKSWMESEFRVYSSANN

CTFEYVSQPFLMDLEGKQGNFKNLREFVFGWTAGAAAYYVGYLQPRTFLL

KYNENGTITDAVDCALDPLSETKCTLKSFTVEKGIYQTSNFRVQPTESIV

RFPNITNLCPFGEVFNATRFASVYAWNRKRISNCVADYSVLYNSASFSTF

KCYGVSPTKLNDLCFTNVYADSFVIRGDEVRQIAPGQTGKIADYNYKLPD

DFTGCVIAWNSNNLDSKVGGNYNYLYRLFRKSNLKPFERDISTEIYQAGS

TPCNGVEGFNCYFPLQSYGFQPTNGVGYQPYRVVVLSFELLHAPATVCGP

KKSTNLVKNKCVNFNFNGLTGTGVLTESNKKFLPFQQFGRDIADTTDAVR

DPQTLEILDITPCSFGGVSVITPGTNTSNQVAVLYQDVNCTEVPVAIHAD

QLTPTWRVYSTGSNVFQTRAGCLIGAEHVNNSYECDIPIGAGICASYQTQ

TNSPRRARAHHHHHHHHH

SBT-502 (SEQ ID NO:3) refers to a recombinant ACE2 protein. (encoded by the human ACE2 (NP 068576.1) (Met1-Ser740)) (Sino Biological US Inc., Wayne, PA). The sequence is as follows:

SEQ ID NO: 3
MSSSSWLLLSLVAVTAAQSTIEEQAKTFLDKFNHEAEDLFYQSSLASWNY

NTNITEENVQNMNNAGDKWSAFLKEQSTLAQMYPLQEIQNLTVKLQLQAL

QQNGSSVLSEDKSKRLNTILNTMSTIYSTGKVCNPDNPQECLLLEPGLNE

IMANSLDYNERLWAWESWRSEVGKQLRPLYEEYVVLKNEMARANHYEDYG

DYWRGDYEVNGVDGYDYSRGQLIEDVEHTFEEIKPLYEHLHAYVRAKLMN

AYPSYISPIGCLPAHLLGDMWGRFWTNLYSLTVPFGQKPNIDVTDAMVDQ

AWDAQRIFKEAEKFFVSVGLPNMTQGFWENSMLTDPGNVQKAVCHPTAWD

LGKGDFRILMCTKVTMDDFLTAHHEMGHIQYDMAYAAQPFLLRNGANEGF

HEAVGEIMSLSAATPKHLKSIGLLSPDFQEDNETEINFLLQALTIVGTLP

FTYMLEKWRWMVFKGEIPKDQWMKKWWEMKREIVGVVEPVPHDETYCDPA

SLFHVSNDYSFIRYYTRTLYQFQFQEALCQAAKHEGPLHKCDISNSTEAG

QKLFNMLRLGKSEPWTLALENVVGAKNMNVRPLLNYFEPLFTWLKDQNKN

SFVGWSTDWSPYADQSIKVRISLKSALGDKAYEWNDNEMYLFRSSVAYAM

RQYFLKVKNQMILFGEEDVRVANLKPRISFNFFVTAPKNVSDIIPRTEVE

KAIRMSRSRINDAFRLNDNSLEFLGIQPTLGPPNQPPVSIWLIVFGVVMG

-continued
VIVVGIVILIFTGIRDRKKKNKARSGENPYASIDISKGENNPGFQNTDDV

QTSF

As used herein, the term "substantially identical" or "substantially homologous" refers to a first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities.

Calculations of "homology" or "identity" between two sequences are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). For substantial identity, the length of a reference sequence aligned for comparison purposes is at least 80%, but can be higher, e.g., at least 85%, 90%, 95%, 96%, 97%, 98%, 99% or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, accounting for the number of gaps, and the length of each gap, which need to be introduced for optimal alignment of the two sequences. The comparison of sequences and determination of percent homology between two sequences are accomplished using a mathematical algorithm.

The compositions of the invention may have additional conservative or non-essential amino acid substitutions, which do not have a substantial effect on the polypeptide functions. Whether or not a particular substitution will be tolerated, i.e., will not adversely affect desired biological properties, such as binding activity, can be determined. A "conservative amino acid substitution" is one in which an amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, Valine, isoleucine) and aromatic side chains (e.g., tyrosine, phenylalanine, tryptophan, histidine).

A "non-essential" amino acid residue is a residue that can be altered from the wild-type sequence of a polypeptide without substantially altering a biological activity, whereas an "essential" amino acid residue results in such a change.

The term "synthetic" refers to production by in vitro chemical or enzymatic synthesis.

The term "target" as used herein refers to any component, antigen, or moiety that is recognized by the protein or polypeptide of the invention. The term "intracellular target" refers to any component, antigen, or moiety present inside a cell. A "transmembrane target" is a component, antigen, or moiety that is located within the cell membrane. An "extracellular target" refers to a component, antigen, or moiety that is located outside of the cell.

A "therapeutic composition" as used herein means a substance that is intended to have a therapeutic effect such as pharmaceutical compositions, genetic materials, biologics, and other substances. Genetic materials include substances intended to have a direct or indirect genetic therapeutic effect such as genetic vectors, genetic regulator elements, genetic structural elements, DNA, RNA and the like. Biologics include substances that are living matter or derived from living matter intended to have a therapeutic effect.

As used herein, the phrases "therapeutically effective amount" and "prophylactically effective amount" refer to an amount that provides a therapeutic benefit in the treatment, prevention, or management of a disease or an overt symptom of the disease. The therapeutically effective amount may treat a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease. The specific amount that is therapeutically effective can be readily determined by an ordinary medical practitioner and may vary depending on factors known in the art, such as, e.g., the type of disease, the patient's history and age, the stage of disease, and the administration of other therapeutic agents.

It is contemplated in the present invention that an isolated viral receptor-binding ligand can be used alone or in combination with the viral receptor-binding ligand's target RBD as a therapeutic to prevent or reduce viral infection in an individual.

The present invention relates to viral proteins and polypeptides directed against cellular receptors. The invention also includes nucleic acids encoding the proteins and polypeptides, and compositions comprising the proteins and peptides of the invention. The invention includes the use of the compositions for prophylactic, therapeutic or diagnostic purposes. It is also contemplated that variants of viral proteins can be used in the present invention.

In addition, the viral proteins and polypeptides of the invention can be constructed as fusion proteins containing a compound, such as a protein, that can be used to extend the serum half-life of the protein for therapeutic applications, such as, for example, albumin, transferrin, and/or Fc-portion of antibodies. The fusion protein can optionally contain a linker portion.

The methods and compositions detailed in the present invention can be used to treat diseases described herein, and can be used with any dosage and/or formulation described herein or otherwise known, as well as with any route of administration described herein or otherwise known to one of skill in the art.

EXAMPLES

Example 1: Inhibition of SARS-CoV-2 and ACE2 Binding

The ability of recombinant proteins to inhibit SARS-CoV-2 S1 protein binding to ACE2 was determined using an enzyme-linked immunosorbent assay (ELISA) in triplicate. The nomenclature used in the experiments is as follows: SBT-500 (SEQ ID NO:1) is the recombinant RBD of the S1 protein (encoded by the SARS-CoV-2 (2019-nCoV) Spike Protein (RBD) (YP_009724390.1) (Arg319-Phe541) expressed with a polyhistidine tag at the C-terminus); SBT-501 (SEQ ID NO:2) refers to the entire recombinant S1 protein (encoded by SARS-CoV-2 spike protein S1 Subunit (YP_009724390.1) DNA sequence (Val16-Arg685) expressed with a polyhistidine tag at the C-terminus); and SBT-502 (SEQ ID NO:3) refers to a recombinant ACE2 protein (encoded by the human ACE2 (NP_068576.1) (Met1-Ser740)).

First, the recombinant protein reagents were reconstituted. 10 µl of 600 µg/mL stock SARS-CoV-2 S1 Protein (Fc Tag) (Acro Biosystems, Newark, DE) solution was diluted with 4 ml Tris Buffered Saline (TBS) (50 mM Tris-HCl, pH 7.6, 150 mM NaCl) to make 1.5 µg/mL S1 protein coat solution. 50 µl of the diluted S1 protein coat solution was added to the wells of a plate containing Nunc® strips (Thermo Fisher Scientific, Waltham, MA). A well containing no S1 protein coating solution was used as a negative control. The strips were incubated at 4° C. for 16 hours or overnight.

The S1 protein coating solution was then removed, and the wells were washed three times with 300 µL of TBS. After the final wash, the plate was inverted and blotted with paper towels.

The wells were blocked with 300 µL of blocking buffer (TBS with 0.5% casein (w/v)) at room temperature for 1.5 hours. The blocking buffer was removed by decanting. The plate was then inverted and blotted with paper towels.

100 µg/mL of biotinylated human ACE2 stock solution (Acro Biosystems) was diluted to 0.12 µg/mL with blocking buffer to make a biotinylated human ACE2 working solution. The final concentration of the biotinylated human ACE2 working solution used in the assay was 0.06 µg/mL.

Serial dilutions of SBT-500, SBT-501, SBT-502, and Anti-SARS-CoV-2 Neutralizing Ab (Human IgG) (positive control) (Acro Biosystems) were made in blocking buffer. The dilutions were as follows:

SBT-500: 20, 6, 2, 0.6, 0.2, 0.06 µg/ml.

SBT-501: 120, 60, 20, 6, 2, 0.6 µg/ml.

SBT-502: 60, 30, 15, 7.5, 3.75 µg/ml.

Anti-SARS-CoV-2 Ab: 60, 20, 6, 2, 0.6, 0.2 µg/ml.

30 µl biotinylated human ACE2 working solution was mixed with 30 µl of the various concentrations of SBT-500, SBT-501, SBT-502 and the Anti-SARS-CoV-2 Ab, which made the final concentrations of the recombinant proteins used in the assay half of the values listed above. 30 µl diluted ACE2 was mixed with 30 µl blocking buffer and used as a negative control. The diluted recombinant proteins were incubated at room temperature for 10 minutes.

50 µl of the diluted recombinant proteins were added to the blocked wells using the schema detailed in Table 1. The wells were then covered and incubated at room temperature for 40 minutes with shaking.

TABLE 1

| | Antibody concentration | | | | | | | | | |
|---|---|---|---|---|---|---|---|---|---|---|
| | Strip # | | | | | | | | | Anti-SARS CoV-2 Ab |
| | SBT-500 (μg/mL) | | | SBT-501 (μg/mL) | | | SBT-502 (μg/mL) | | | (μg/mL) |
| Well | 1 | 2 | 3 | 4 | 5 | 6 | 7 | 8 | 9 | 10 |
| A | 10 | 10 | 10 | 60 | 60 | 60 | 30 | 30 | 30 | 30 |
| B | 3 | 3 | 3 | 30 | 30 | 30 | 15 | 15 | 15 | 10 |
| C | 1 | 1 | 1 | 10 | 10 | 10 | 7.5 | 7.5 | 7.5 | 3 |
| D | 0.3 | 0.3 | * | * | 3 | 3 | 3.75 | 3.75 | 3.75 | 1 |
| E | 0.1 | 0.1 | 0.1 | 1 | 1 | 1 | 1.875 | 1.875 | 1.875 | 0.3 |
| F | 0.03 | 0.03 | 0.03 | 0.3 | 0.3 | 0.3 | 0 | 0 | 0 | 0.1 |
| G | 0 | 0 | 0 | 0 | 0 | 0 | — | — | — | 0 |
| H | — | — | — | — | — | — | — | — | — | 0 ** |

*No data
** Uncoated well

The solution was then removed from the wells, and the wells were washed three times as follows: 300 μL of TBST (TBS with 0.05% (v/v) Tween-20 (pH7.4)) was added to each well, the plate was tapped gently for 1 minute, and remaining buffer was removed by decanting. The plate was then inverted and blotted against paper towels. The wells were then washed twice with TBS.

A 0.1 μg/mL Streptavidin-HRP working solution was made by dilution of a Streptavidin-HRP stock solution (50 μg/mL) with blocking buffer. 50 μL of the Streptavidin-HRP working solution was added to each well. The plate was then covered and incubated at room temperature for 30 minutes with shaking. After 30 minutes, the wells were washed as described above.

Following the wash, 50 μL Pierce® TMB Substrate (Thermo Fisher Scientific) was added to each well and incubated at room temperature for 15 minutes with shaking.

50 μL of a 2M HCl stop solution was then added to each well. The plate was shaken briefly to mix. The absorbance of the wells at 450 nm was measured using a UV/Vis microplate spectrophotometer and is shown in Table 2.

TABLE 2

| | Absorbance of ELISA | | | | | | | | | |
|---|---|---|---|---|---|---|---|---|---|---|
| | Strip # | | | | | | | | | Anti-SARS CoV-2 Ab |
| | SBT-500 | | | SBT-501 | | | SBT-502 | | | |
| Well | 1 | 2 | 3 | 4 | 5 | 6 | 7 | 8 | 9 | 10 |
| A | 0.047 | 0.050 | 0.048 | 0.044 | 0.043 | 0.045 | 0.081 | 0.082 | 0.079 | 0.043 |
| B | 0.070 | 0.065 | 0.063 | 0.049 | 0.046 | 0.048 | 0.096 | 0.099 | 0.097 | 0.053 |
| C | 0.111 | 0.107 | 0.101 | 0.064 | 0.063 | 0.065 | 0.118 | 0.137 | 0.125 | 0.067 |
| D | 0.259 | 0.249 | * | * | 0.120 | 0.130 | 0.176 | 0.165 | 0.150 | 0.094 |
| E | 0.408 | 0.432 | 0.354 | 0.266 | 0.257 | 0.271 | 0.245 | 0.269 | 0.216 | 0.250 |
| F | 0.593 | 0.543 | 0.580 | 0.365 | 0.318 | 0.381 | 0.446 | 0.546 | 0.542 | 0.225 |
| G | 0.767 | 0.797 | 0.594 | 0.544 | 0.567 | 0.585 | — | — | — | 0.538 |
| H | — | — | — | — | — | — | — | — | — | 0.042 |

*No data

TABLE 3

| Average absorbance values | | | | | | | | | | | |
|---|---|---|---|---|---|---|---|---|---|---|---|
| SBT-500 | | | SBT-501 | | | SBT-502 | | | anti-SARS-CoV-2 | | |
| ug/ml | OD450 | SD | ug/ml | OD450 | SD | ug/ml | OD450 | SD | ug/ml | OD450 | |
| 10 | 0.049 | 0.001312 | 60 | 0.044 | 0.000777 | 30 | 0.081 | 0.001728 | 30 | 0.043 | |
| 3 | 0.066 | 0.003892 | 30 | 0.048 | 0.001802 | 15 | 0.097 | 0.001462 | 10 | 0.053 | |
| 1 | 0.106 | 0.004993 | 10 | 0.064 | 0.001279 | 7.5 | 0.127 | 0.009225 | 3 | 0.067 | |
| 0.3 | 0.254* | 0.006616 | 3 | 0.125* | 0.006923 | 3.75 | 0.164 | 0.01298 | 1 | 0.094 | |
| 0.1 | 0.398 | 0.04 | 1 | 0.265 | 0.007235 | 1.875 | 0.243 | 0.026838 | 0.3 | 0.250 | |
| 0.03 | 0.572 | 0.026078 | 0.3 | 0.355 | 0.032403 | 0 | 0.511 | 0.056166 | 0.1 | 0.225 | |
| 0 | 0.719 | 0.109466 | 0 | 0.565 | 0.020498 | | | | 0 | 0.538 | |

* Average of 2 values

FIG. 1 shows a graphical representation of average absorbance values from Table 3. As can be seen, SBT-500, SBT-501, and SBT-502 block the interaction of the SARS-CoV-2 S1 protein to ACE2 receptor.

Example 2: In Vitro Inhibition of SARS-CoV-2 and ACE2 Binding

The ability of SBT-500 and SBT-501 alone or in combination to inhibit SARS-CoV-2 infection in vitro was determined.

The ACE2-HEK293 cell line (BPS Bioscience, Inc., San Diego, CA) is a recombinant, clonally stable HEK293 cell line that constitutively expresses full length human ACE2. ACE2-HEK293 cells were maintained and assayed in DMEM (Corning Inc.) containing 10% Fetal Bovine Serum (ATCC Manassas, VA), 0.5 µg/ml Puromycin (Selleckchem, Houston, TX), and 1% Penicillin/Streptomycin (Gibco, Thermo Fisher Scientific).

A pseudovirus, namely a SARS-CoV-2 Spike (D614G) lentivirus (BPS Bioscience Inc.), that expresses the SARS-Cov-2 Spike protein was used in the assays. The SARS-CoV-2 Spike (D614G) lentivirus contains the SARS-CoV-2 Spike (Genbank Accession #QHD43416.1; with D614G mutation) as the envelope glycoproteins. The pseudovirions also contains a firefly luciferase gene driven by a CMV promoter, which allows spike-mediated cell entry to be measured via luciferase activity.

The SARS-CoV-2 pseudovirus Spike protein recognizes and attaches to the ACE2 receptor of the ACE2-HEK293 cell. Once the SARS-CoV-2 pseudovirus enters the ACE2-HEK293 cell, the luciferase activity is measured. Compounds can be tested for the ability to inhibit binding of the SARS-CoV-2 pseudovirus to the ACE2 receptor. If a compound blocks binding of the SARS-CoV-2 pseudovirus to the ACE2 receptor on the ACE2-HEK293 cells, then the luciferase activity is decreased.

For the following experiments, a human monoclonal antibody, anti-SARS-CoV-2 Neutralizing Ab (Acro Biosystems) that binds the Spike protein and significantly inhibits the ability of the SARS-CoV-2 pseudovirus to bind to the ACE2 receptor was used as a positive control.

Figure 2:
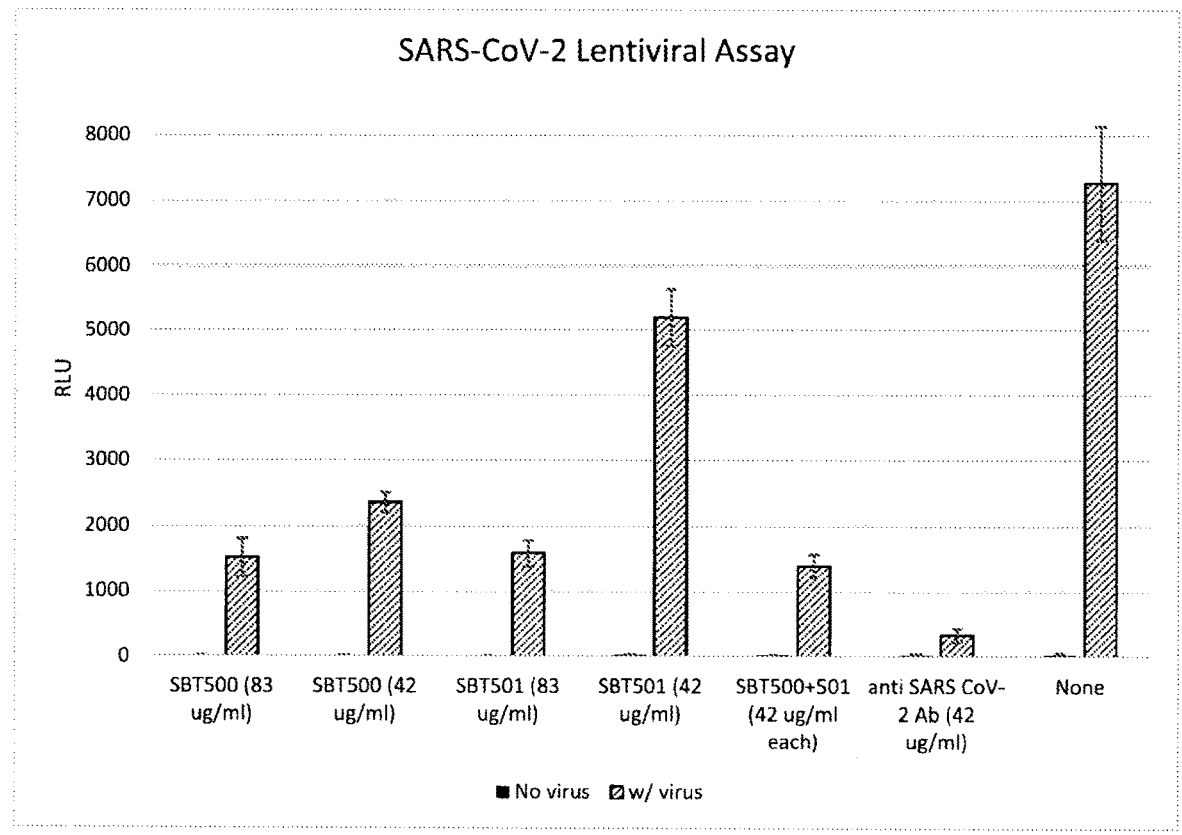
FIG. 2 depicts the average RLU values from Table 4.

ACE2-HEK293 cells were seeded at a density of 5,000-10,000 cells per well into 60 wells of a white clear-bottomed 96-well plate (Corning, Inc., Corning, NY) and incubated overnight at 37° C. with 5% $CO_2$. The experiments were run in triplicate. 5 µl of various concentrations of SBT-500, SBT-501, a combination of SBT-500 and SBT-501, and anti-SARS-CoV-2 Ab (used as a positive control), were mixed with 5 µl growth medium or SARS-CoV-2 pseudovirus and then added to the appropriate wells. Growth medium alone was used as a negative control. The plates were then incubated for 50-58 hours, and were assayed for luminescence, as measured in relative light units (RLU), using the One-Step™ Luciferase Assay System (BPS Bioscience) following the manufacturer's protocol. The results are shown in Table 4 and FIG. 2.

TABLE 4

Luciferase activity as measured in relative light units

| Compound | Average Relative Light Units (RLU) | | Standard Deviation | |
|---|---|---|---|---|
| | No virus | w/ virus | No virus | w/ virus |
| SBT-500 (83 ug/ml) | 20 | 1512 | 4 | 294 |
| SBT-500 (42 ug/ml) | 22 | 2354 | 2 | 151 |

TABLE 4-continued

Luciferase activity as measured in relative light units

| Compound | Average Relative Light Units (RLU) | | Standard Deviation | |
|---|---|---|---|---|
| | No virus | w/ virus | No virus | w/ virus |
| SBT-501 (83 ug/ml) | 19 | 1580 | 3 | 198 |
| SBT-501 (42 ug/ml) | 24 | 5200 | 15 | 438 |
| SBT-500 + SBT-501 (42 ug/ml each) | 26 | 1389 | 6 | 174 |
| anti-SARS-CoV-2 Ab (42 ug/ml) | 30 | 337 | 14 | 106 |
| None | 31 | 7262 | 21 | 874 |

Figure 3:
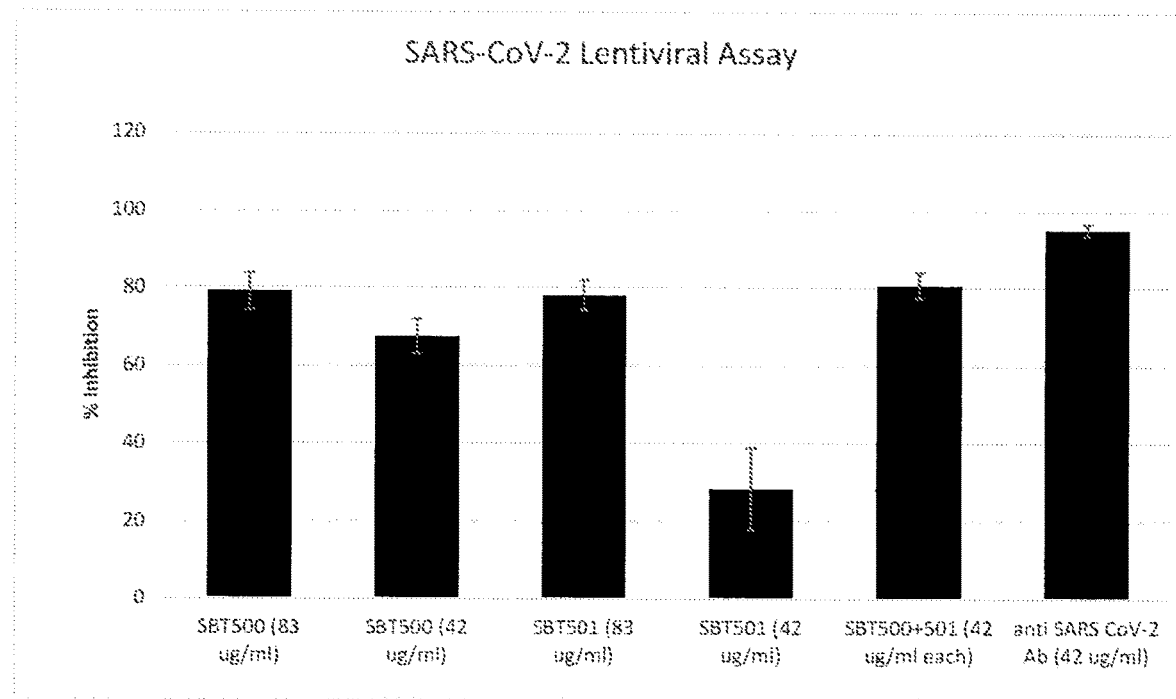
FIG. 3 depicts the average RLU values from Table 5.

The results of the inhibition of the SARS-CoV-2 pseudovirus to bind to the ACE2 receptor with SBT-500 and SBT-501 alone or in combination are shown in Table 5 and FIG. 3.

TABLE 5

Inhibition of SARS-COV-2 pseudovirus binding to ACE2-HEK293 cells.

| Compound | Average RLU/Control RLU | Standard Deviation | % Inhibition | Standard Deviation |
|---|---|---|---|---|
| SBT-500 (83 ug/ml) | 0.21 | 0.047562 | 79 | 5 |
| SBT-500 (42 ug/ml) | 0.32 | 0.04421 | 68 | 4 |
| SBT-501 (83 ug/ml) | 0.22 | 0.037852 | 78 | 4 |
| SBT-501 (42 ug/ml) | 0.72 | 0.105248 | 28 | 11 |
| SBT-500 + SBT-501 (42 ug/ml each) | 0.19 | 0.033278 | 81 | 3 |
| Anti-SARS-COV-2 Ab (42 ug/ml) | 0.05 | 0.015594 | 95 | 2 |

The results show that SBT-500 and SBT-501 can inhibit SARS-CoV-2 entry into cells containing the ACE2 receptor in a dose-dependent manner. The combination of SBT-500 and SBT-501 also inhibits SARS-CoV-2 entry into cells containing the ACE2 receptor. The combination therapy approaches the percent inhibition of the positive control (~95%) versus 80% for SBT-500+SBT-501. Thus, SBT-500, SBT-501, SBT-502 can be used alone or in combination to prevent or reduce infection with SARS-CoV-1 and/or SARS-CoV-2, as well as preventing or reduction infection with SARS-CoV-1 and SARS-CoV-2 variants.

Figure 4:
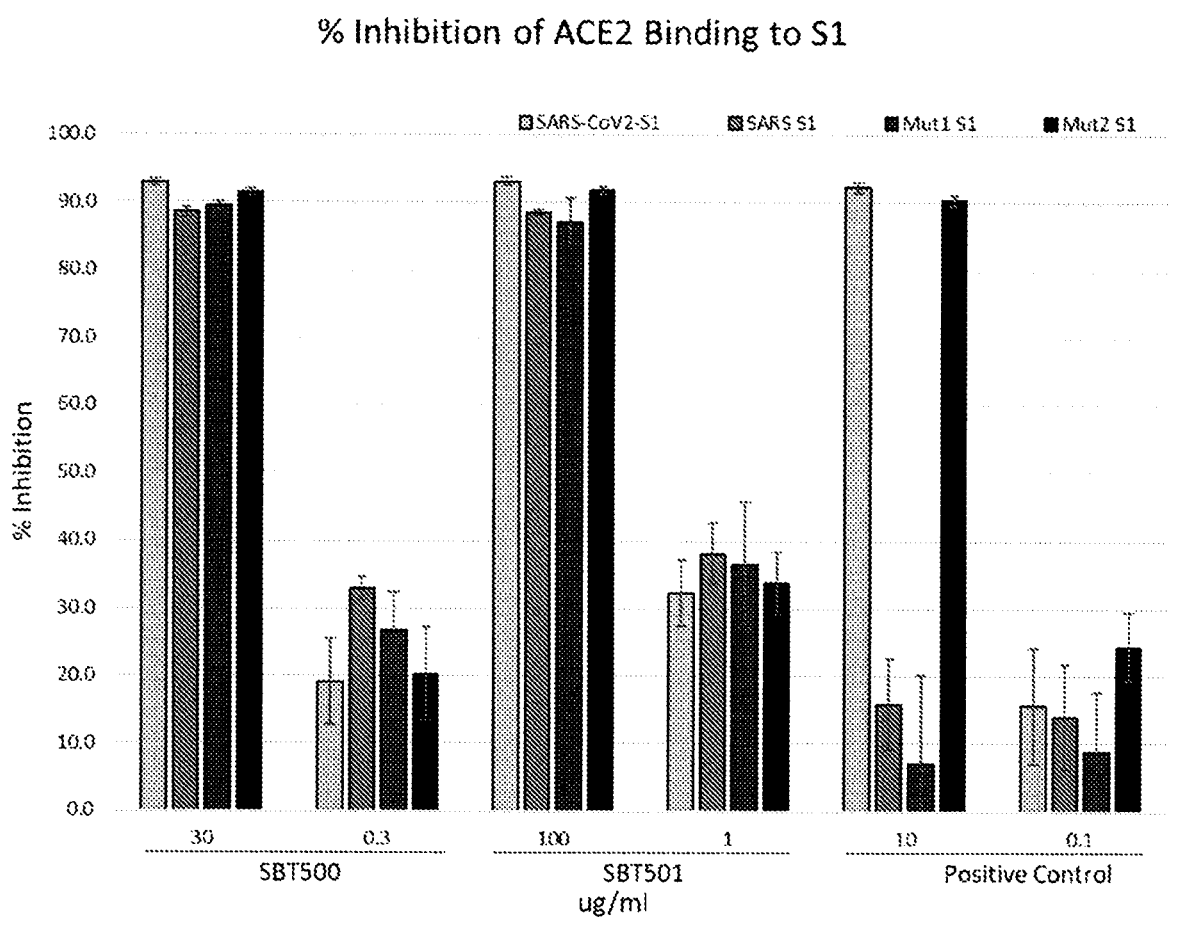

Example 3: SBT-500 and SBT-501 Inhibits Binding of the Spike Protein from the SARS-1 Virus, SARS-CoV-2 Virus, UK-Variant and the South African Variant ELISA assays were done as described above in Example 2 to assess the percent inhibition of ACE2 binding to various Spike proteins. In this experiment, fusion proteins were made containing albumin linked to SBT-500 and SBT-501 at the C-terminus. As can be seen in FIG. 4, SBT-500 and SBT-501 inhibits binding of the Spike protein from the SARS-1 virus, SARS-CoV-2 virus, UK-variant and the South African variant. Mut1 refers to the UK variant of SARS-CoV-2 (2019-nCoV) containing mutations in the Spike protein (K417N, E484K, N501Y, D614G). Mut2 refers to the South African variant of SARS-CoV-2 (2019-nCoV) Spike protein (DHV69-70, DY144, N501Y, A570D, D614G, P681H). The positive control was a monoclonal antibody to the SARS-CoV-2 Spike protein derived from an infected patient. The degree of inhibition for SARS-1 and the UK-variant is greater with SBT-500 and SBT-501 then the positive control antibody. These results demonstrate that SBT-500 and SBT-501 can be administered to a subject to treat or prevent infection with coronavirus variants.

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure. All references cited herein are incorporated by reference in their entirety.

What is claimed is:

1. A method for treating infection with severe acute respiratory syndrome coronavirus 1 (SARS-CoV-1), severe acute respiratory syndrome coronavirus 2 (SARS-CoV-2) or a variant thereof, wherein the method comprises administering to a subject in need thereof a composition comprising a first polypeptide and a second polypeptide, wherein the first polypeptide consists of SEQ ID NO:1 or SEQ ID NO:1 linked to albumin, transferrin, or Fc-portion of an antibody, and the second polypeptide comprises SEQ ID NO:2.

2. The method of claim 1, wherein the composition further comprises a pharmaceutically acceptable carrier or excipient.

3. The method of claim 1, wherein the composition is administered by a route selected from the group consisting of oral, intravenous, intramuscular, subcutaneous, and transdermal administration.

4. The method of claim 1, wherein the second polypeptide is further linked to a compound that extends the serum half-life of the second polypeptide.

5. The method of claim 4, wherein the compound is albumin, transferrin, or Fc-portion of an antibody.

* * * * *

```
                           SEQUENCE LISTING

Sequence total quantity: 3
SEQ ID NO: 1             moltype = AA  length = 233
FEATURE                  Location/Qualifiers
REGION                   1..233
                         note = Synthesized
source                   1..233
                         mol_type = protein
                         organism = synthetic construct
SEQUENCE: 1
RVQPTESIVR FPNITNLCPF GEVFNATRFA SVYAWNRKRI SNCVADYSVL YNSASFSTFK    60
CYGVSPTKLN DLCFTNVYAD SFVIRGDEVR QIAPGQTGKI ADYNYKLPDD FTGCVIAWNS   120
NNLDSKVGGN YNYLYRLFRK SNLKPFERDI STEIYQAGST PCNGVEGFNC YFPLQSYGFQ   180
PTNGVGYQPY RVVVLSFELL HAPATVCGPK KSNLVKNKCV NFAHHHHHHH HHH          233

SEQ ID NO: 2             moltype = AA  length = 681
FEATURE                  Location/Qualifiers
REGION                   1..681
                         note = Synthesized
source                   1..681
                         mol_type = protein
                         organism = synthetic construct
SEQUENCE: 2
VNLTTRTQLP PAYTNSFTRG VYYPDKVFRS SVLHSTQDLF LPFFSNVTWF HAIHVSGTNG    60
TKRFDNPVLP FNDGVYFAST EKSNIIRGWI FGTTLDSKTQ SLLIVNNATN VVIKVCEFQF   120
CNDPFLGVYY HKNNKSWMES EFRVYSSANN CTFEYVSQPF LMDLEGKQGN FKNLREFVFK   180
NIDGYFKIYS KHTPINLVRD LPQGFSALEP LVDLPIGINI TRFQTLLALH RSYLTPGDSS   240
SGWTAGAAAY YVGYLQPRTF LLKYNENGTI TDAVDCALDP LSETKCTLKS FTVEKGIYQT   300
SNFRVQPTES IVRFPNITNL CPFGEVFNAT RFASVYAWNR KRISNCVADY SVLYNSASFS   360
TFKCYGVSPT KLNDLCFTNV YADSFVIRGD EVRQIAPGQT GKIADYNYKL PDDFTGCVIA   420
WNSNNLDSKV GGNYNYLYRL FRKSNLKPFE RDISTEIYQA GSTPCNGVEG FNCYFPLQSY   480
GFQPTNGVGY QPYRVVVLSF ELLHAPATVC GPKKSTNLVK NKCVNFNFNG LTGTGVLTES   540
NKKFLPFQQF GRDIADTTDA VRDPQTLEIL DITPCSFGGV SVITPGTNTS NQVAVLYQDV   600
NCTEVPVAIH ADQLTPTWRV YSTGSNVFQT RAGCLIGAEH VNNSYECDIP IGAGICASYQ   660
TQTNSPRRAR AHHHHHHHHH H                                             681

SEQ ID NO: 3             moltype = AA  length = 805
FEATURE                  Location/Qualifiers
REGION                   1..805
                         note = Synthesized
source                   1..805
                         mol_type = protein
                         organism = synthetic construct
SEQUENCE: 3
MSSSSWLLLS LVAVTAAQST IEEQAKTFLD KFNHEAEDLF YQSSLASWNY NTNITEENVQ    60
NMNNAGDKWS AFLKEQSTLA QMYPLQEIQN LTVKLQLQAL QQNGSSVLSE DKSKRLNTIL   120
NTMSTIYSTG KVCNPDNPQE CLLLEPGLNE IMANSLDYNE RLWAWESWRS EVGKQLRPLY   180
EEYVVLKNEM ARANHYEDYG DYWRGDYEVN GVDGYDYSRG QLIEDVEHTF EEIKPLYEHL   240
HAYVRAKLMN AYPSYISPIG CLPAHLLGDM WGRFWTNLYS LTVPFGQKPN IDVTDAMVDQ   300
AWDAQRIFKE AEKFFVSVGL PNMTQGFWEN SMLTDPGNVQ KAVCHPTAWD LGKGDFRILM   360
CTKVTMDDFL TAHHEMGHIQ YDMAYAAQPF LLRNGANEGF HEAVGEIMSL SAATPKHLKS   420
IGLLSPDFQE DNETEINFLL KQALTIVGTL PFTYMLEKWR WMVFKGEIPK DQWMKKWWEM   480
KREIVGVVEP VPHDETYCDP ASLFHVSNDY SFIRYYTRTL YQFQFQEALC QAAKHEGPLH   540
KCDISNSTEA GQKLFNMLRL GKSEPWTLAL ENVVGAKNMN VRPLLNYFEP LFTWLKDQNK   600
NSFVGWSTDW SPYADQSIKV RISLKSALGD KAYEWNDNEM YLFRSSVAYA MRQYFLKVKN   660
QMILFGEEDV RVANLKPRIS FNFFVTAPKN VSDIIPRTEV EKAIRMSRSR INDAFRLNDN   720
SLEFLGIQPT LGPPNQPPVS IWLIVFGVVM GVIVVGIVIL IFTGIRDRKK KNKARSGENP   780
YASIDISKGE NNPGFQNTDD VQTSF                                         805
```